United States Patent
O'Brien, Jr. et al.

(10) Patent No.: US 8,790,414 B2
(45) Date of Patent: Jul. 29, 2014

(54) GRAFT FOR HYSTEROTOMY CLOSURE

(75) Inventors: John Michael O'Brien, Jr., Lexington, KY (US); Daniel K. Whetham, Bloomington, IN (US); Michael Hiles, Lafayette, IN (US)

(73) Assignees: Cook Biotech Incorporated, West Lafayette, IN (US); Cook Medical Technologies LLC, Bloomington, IN (US)

( * ) Notice: Subject to any disclaimer, the term of this patent is extended or adjusted under 35 U.S.C. 154(b) by 1734 days.

(21) Appl. No.: 11/938,070

(22) Filed: Nov. 9, 2007

(65) Prior Publication Data

US 2008/0114469 A1    May 15, 2008

Related U.S. Application Data

(60) Provisional application No. 60/865,243, filed on Nov. 10, 2006.

(51) Int. Cl.
*A61F 2/02*  (2006.01)

(52) U.S. Cl.
USPC ............................................ 623/23.72

(58) Field of Classification Search
CPC ............ A61B 17/08; A61B 2019/4878; A61F 2/0063; A61F 2210/0004
USPC .............................. 606/151; 623/23.72–23.74
See application file for complete search history.

(56) References Cited

U.S. PATENT DOCUMENTS

| | | | |
|---|---|---|---|
| 3,557,795 A * | 1/1971 | Hirsch ........................ | 606/228 |
| 5,380,299 A | 1/1995 | Fearnot et al. | |
| 5,516,533 A | 5/1996 | Badylak et al. | |
| 5,755,791 A * | 5/1998 | Whitson et al. ............... | 623/1.1 |
| 5,866,414 A | 2/1999 | Badylak et al. | |
| 5,968,096 A * | 10/1999 | Whitson et al. ............... | 424/423 |
| 5,997,575 A * | 12/1999 | Whitson et al. ............... | 623/1.1 |
| 6,113,623 A | 9/2000 | Sgro | |
| 6,206,931 B1 | 3/2001 | Cook et al. | |
| 6,530,951 B1 | 3/2003 | Bates et al. | |
| 6,774,278 B1 | 8/2004 | Ragheb et al. | |
| 2002/0098278 A1 | 7/2002 | Bates et al. | |
| 2003/0028243 A1 | 2/2003 | Bates et al. | |
| 2003/0036794 A1 | 2/2003 | Ragheb et al. | |
| 2003/0051735 A1 | 3/2003 | Pavcnik et al. | |

(Continued)

FOREIGN PATENT DOCUMENTS

| | | |
|---|---|---|
| EP | 1 421 916 | 5/2004 |
| WO | WO 95/25482 | 9/1995 |
| WO | WO 00/44394 | 8/2000 |
| WO | WO 2005/020847 A2 | 3/2005 |

OTHER PUBLICATIONS

International preliminary report on patentability dated May 22, 2009 for corresponding PCT/US2007/084201.

(Continued)

*Primary Examiner* — Corrine M McDermott
*Assistant Examiner* — Son Dang
(74) *Attorney, Agent, or Firm* — Brinks Gilson & Lione

(57) ABSTRACT

A graft and method of using a graft are described that should decrease the incidence of abnormal placentation and uterine rupture that result from cesarean section and restore the anatomic integrity of the uterus at a hysterotomy surgical site, while not disturbing the involution of the postpartum uterus.

7 Claims, 8 Drawing Sheets

(56) References Cited

U.S. PATENT DOCUMENTS

| | | | |
|---|---|---|---|
| 2004/0068241 | A1 | 4/2004 | Fischer, Jr. |
| 2004/0073284 | A1 | 4/2004 | Bates et al. |
| 2004/0180042 | A1 | 9/2004 | Cook et al. |
| 2005/0021141 | A1 | 1/2005 | Bleyer et al. |
| 2005/0155608 | A1 | 7/2005 | Pavcnik et al. |
| 2005/0187604 | A1 | 8/2005 | Eells et al. |
| 2005/0222661 | A1 | 10/2005 | Case et al. |
| 2006/0116548 | A1 | 6/2006 | Case et al. |
| 2006/0147433 | A1 | 7/2006 | Hiles |
| 2006/0210597 | A1 | 9/2006 | Hiles |
| 2006/0235511 | A1 | 10/2006 | Osborne |
| 2006/0246033 | A1 | 11/2006 | Ninan |
| 2007/0082060 | A1 | 4/2007 | Hiles et al. |

OTHER PUBLICATIONS

Cook SIS Technology—Surgisis® Soft-Tissue Graft—Overview—obtained at Internet address http://cooksis.com/products/surgisis/index.html, Copyright © Cook Biotech Incorporated 2004, 1 page.

Cook SIS Technology—Scientific Information—Introduction—obtained at Internet address http://cooksis.com/sci/index.html, Copyright © Cook Biotech Incorporated 2004, 2 pages.

Cook SIS Technology—Scientific Information—Tissue Repair: Challenges & Complications—obtained at Internet address http://cooksis.com/sci/tech.html, Copyright © Cook Biotech Incorporated 2004, 2 pages.

Cook SIS Technology—Scientific Information—Mechanism of Action—obtained at Internet address http://cooksis.com/sci/tech2_flash.html, Copyright © Cook Biotech Incorporated 2004, 1 page.

Cook SIS Technology—Scientific Information—Safety—obtained at Internet address http://cooksis.com/sci/tech3.html, Copyright © Cook Biotech Incorporated 2004, 2 pages.

Cook SIS Technology—Scientific Information—Versatility—obtained at Internet address http://cooksis.com/sci/tech4.html, Copyright © Cook Biotech Incorporated 2004, 2 pages.

Cook SIS Technology—Scientific Information—Clinical References—obtained at Internet address http://cooksis.com/sci/ref1.html, Copyright © Cook Biotech Incorporated 2004, 7 pages.

Cook SIS Technology—Surgisis® Soft-Tissue Graft—Ordering Information—obtained at Internet address http://cooksis.com/products/surgisis/order.html, Copyright © Cook Biotech Incorporated 2004, 4 pages.

Cook SIS Technology—Surgisis® Soft-Tissue Graft—Instructions for Use—obtained at Internet address http://cooksis.com/products/surgisis/ifu.html, Copyright © Cook Biotech Incorporated 2005, 3 pages.

Butnariu-Ephrat, M. et al., "Resurfacing of Goat Articular Cartilage by Chondrocytes Derived From Bone Marrow," Clinical Orthopaedics and Related Research, No. 330, Copyright © 1996, by Lippincott-Raven Publishers, pp. 234-243.

PCT Search Report and Written Opinion dated Apr. 9, 2008 for corresponding PCT/US2007/084201.

\* cited by examiner

US 8,790,414 B2

GRAFT FOR HYSTEROTOMY CLOSURE

RELATED APPLICATION

The present patent document claims the benefit of the filing date under 35 U.S.C. §119(e) of Provisional U.S. Patent Application Ser. No. 60/865,243, filed Nov. 10, 2006, which is hereby incorporated by reference in its entirety.

FIELD OF THE INVENTION

The invention relates to medical closures for surgical incisions.

BACKGROUND OF THE INVENTION

Many serious complications may occur after a female gives birth by cesarean section and then becomes pregnant again. Some of these complications are caused by full-thickness defects in the uterine wall at the hysterotomy closure site. These complications include abnormal placentation and uterine rupture at the hysterotomy closure site.

Of the various types of abnormal placentation, there are three notable types including: placenta accreta, placenta previa, and placenta percreta. Placenta accreta is a condition where the placenta abnormally attaches itself to the surface of the uterine wall and has grown into the myometrium-the muscle of the uterine wall. Placenta previa is a condition wherein the placental attachment site extends into the lower uterine segment and can grow to cover the internal cervical os; this condition poses a serious complication for normal vaginal delivery. Placenta percreta is a condition wherein the placenta grows through the uterine wall and into the abdominal cavity. Because the placenta is such a fast growing organ, once into the adnominal cavity, the placenta poses the risk of attaching to the bladder, rectum, bowl, or other nearby organs.

Each type of abnormal placentation poses risk to both the mother and the fetus. First, the mother risks hemorrhaging should the integrity of the placenta be disrupted in such a manner that causes the vessels connecting the placenta to the uterine wall to rupture or detach. The fetus is also at risk because such complications may cause miscarriage, abnormal fetal growth, oligohydramnios, force preterm delivery, or intrauterine fetal death.

The incidence of abnormal placentation and uterine rupture at the hysterotomy closure cite increase as the number of cesarean sections the mother has increases. The correlation between the abnormal placentation and uterine rupture with cesarean are linked to the fact that hysterotomy closures fail to restore the integrity of the pre-hysterotomy uterus. The compromised site that can result in abnormal placentation or uterine rupture often means vaginal birth after cesarean will not be successful; therefore, the mother will need to undergo another cesarean delivery.

What is needed is an apparatus and method to decrease the incidence of abnormal placentation and uterine rupture that result from cesarean section. What is also needed is an apparatus and method for restoring the anatomic integrity of the uterus at the hysterotomy surgical site. Additionally, what is needed is an apparatus and method for reconnecting uterine tissue in such a way so as not to disturb the involution of the postpartum uterus that occurs over the initial six-weeks of postpartum.

BRIEF SUMMARY OF THE INVENTION

A first aspect of the invention includes a graft, wherein the graft includes at least one suitable collagenous material, and the suitable collagenous material is capable of remodeling.

Another aspect of the invention includes a method for repairing a wound site. The method includes providing a graft, wherein the graft includes at least one suitable collagenous material. The suitable collagenous material is capable of remodeling. The method further includes placing the graft in communication with a wound site, attaching the graft to the wound site, and closing the wound site.

Further, another aspect of the invention includes a method for repairing a wound site. The method includes providing a graft, wherein the graft includes at least one suitable collagenous material. The suitable collagenous material is capable of remodeling and the suitable collagenous material includes a suspension gel or a foam tube. The method further includes placing the graft in communication with a wound site and closing the wound site.

BRIEF DESCRIPTION OF THE SEVERAL VIEWS OF THE DRAWINGS

The embodiments will be further described in connection with the attached drawing figures. It is intended that the drawings included as a part of this specification be illustrative of the embodiments and should in no way be considered as a limitation on the scope of the invention.

DETAILED DESCRIPTION OF PRESENTLY PREFERRED EMBODIMENTS

Figure 1:
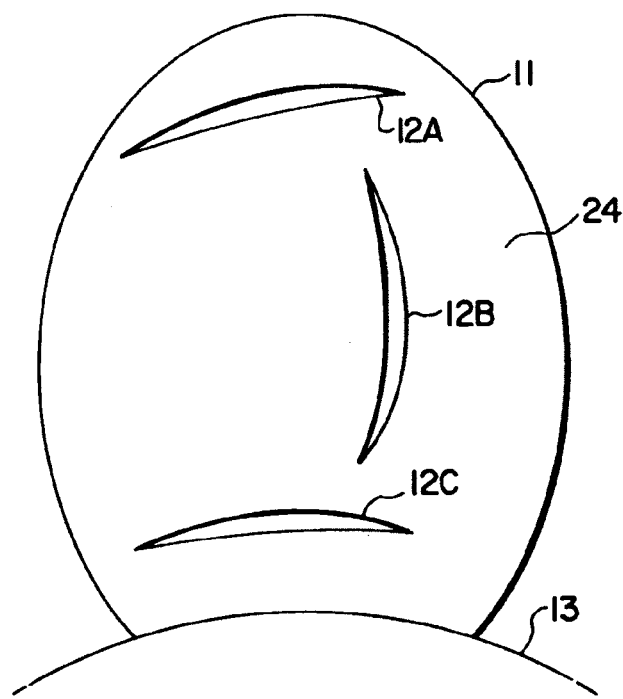
FIG. 1 is a side-view of a postpartum uterus after cesarean.

The exemplary embodiments disclosed herein provide an apparatus that is suitable for implantation into an incision site of a patient to promote strong wound repair. The patient may include both human and veterinary patients.

A more detailed description of the embodiments will now be given with reference to FIGS. 1-18. Throughout the disclosure, like reference numerals and letters refer to like elements. The present invention is not limited to the embodiments illustrated; to the contrary, the present invention specifically contemplates other embodiments not illustrated but intended to be included in the claims.

FIG. 1 is a side-view of uterus 11 with bladder 13 pushed up and away from uterus 11. When a cesarean is performed, the doctor will normally deliver the baby from incision site 12C. However, depending on how severe is the abnormal placentation, the doctor may not be able to use incision site 12C due to placental obstruction. A doctor may be hesitant to push the placenta (not shown) away from the desired incision site due to the dense vascularity of the placenta. Because the placenta contains arterial attachments, there is a high-risk of maternal hemorrhage and exsanguination should any placental-arterial sites be ruptured or disturbed. Therefore, the doctor may choose to use an alternative incision site, 12A, 12B, or others not shown, in order to deliver the baby.

Figure 2:
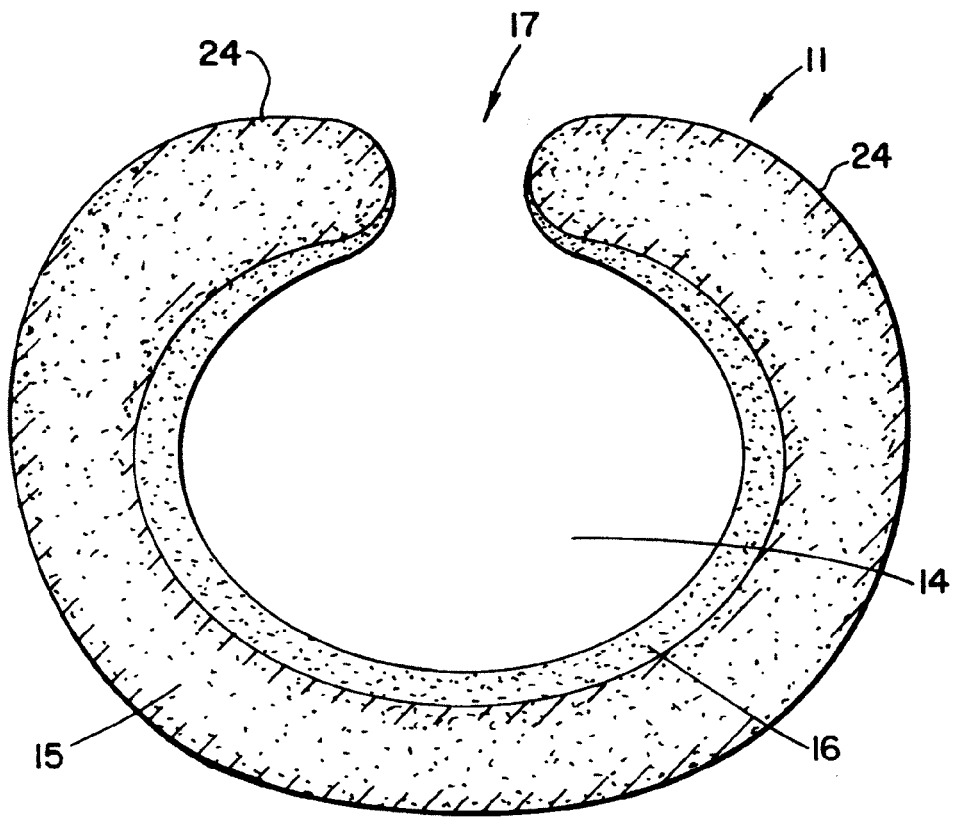
FIG. 2 is a cross-sectional side-view of a uterus after cesarean.

FIG. 2 is a cross-sectional side-view of uterus 11 after having undergone a cesarean and depicts a bodily wall, wherein the incision created a first incised tissue face and a second incised tissue face, the bodily wall having a first surface and a second, opposite surface. In order to deliver the baby, a cut 17 into uterus 11 including visceral peritoneal 24, endometrium 16, and myometrium 15 was made. Hysterotomy site 17 is depicted open to uterine cavity 14 after delivering a baby.

Figure 3:
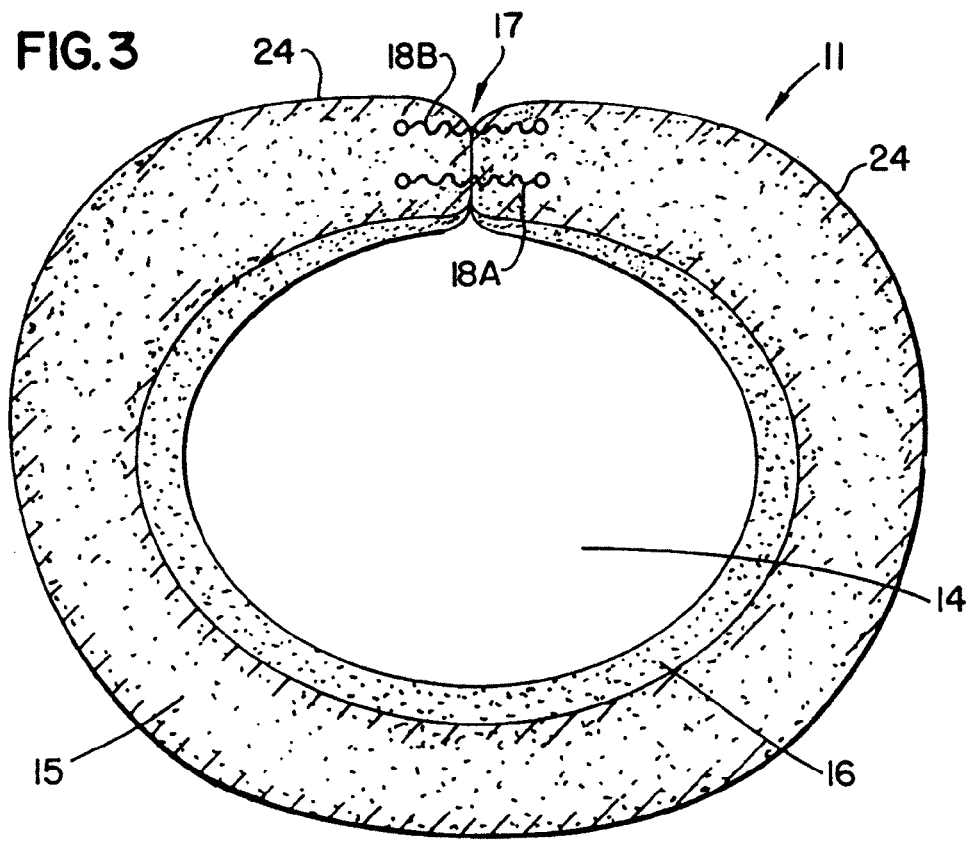
FIG. 3 is a cross-sectional side-view of a uterus after with a typical two-layer hysterotomy closure.

FIG. 3 is cross-sectional side-view of uterus 11 after having a typical two-layer closure performed at hysterotomy site 17. After delivering the baby, the physician closes hysterotomy site 17 normally using a two-layer running-stitch closure (although other types of closures are contemplated, including a single-layer closure and a three or more layer closure). A two-layer closure is preferred because it tends to be stronger than a single-layer closure. However, depending on the mother's needs, a single-layer closure may be preferred in order to prevent hemorrhage from the hysterotomy site. Although some doctors may use a single-layer closure for all patients, most doctors typically use a two-layer closure and a running-stitch suture to reattach the native uterine cells to other native uterine cells in order to limit formation of full-thickness defects and scarring. The first layer of suture 18A is used to close about two-thirds of the defect, the remaining myometrium 15 and visceral peritoneum 24 is closed using the second-layer suture 18B. However, whether using a one or two-layer traditional closing technique, the resulting closure results in a devascularized surgical site that can rupture or be penetrated by the placenta.

Two running-stitch sutures 18A, 18B were used to reconnect the uterine tissue 15, 16. Although running-stitch sutures are shown, other types of sutures can also be used, including but not limited to, a locking-stitch suture. Running-stitch sutures are normally preferred because a running-stitch suture allows for greater blood flow to healing tissue than does a locking-stitch suture. Although a running-stitch suture is generally weaker than a locking-stitch suture, the locking-stitch generally creates more scare tissue resulting in a greater devascularized hysterotomy site. This devascularized site often encourages more scar tissue growth resulting in a hysterotomy closure site that is not as strong as the surrounding uncut uterine cells. Scar tissue is also undesired because it can grow and fuse itself to other organs in the abdominal cavity, thus creating intraperitoneal adhesions. Therefore, although the embodiments herein depict using a two-layer running stitch closure, it is contemplated throughout the disclosure that different amounts of stitch layers maybe used with different types of stitches. Additionally, different methods for closing the site are also contemplated, including but not limited to, using one or more staples or glue.

Figure 4A:
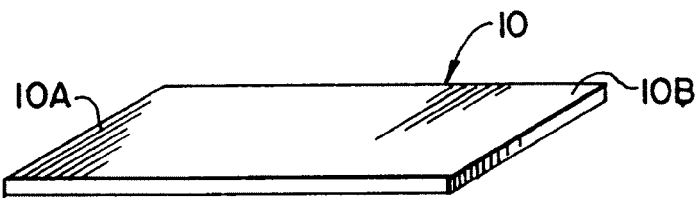
FIG. 4A is a perspective view of an embodiment of the device.
Figure 5:
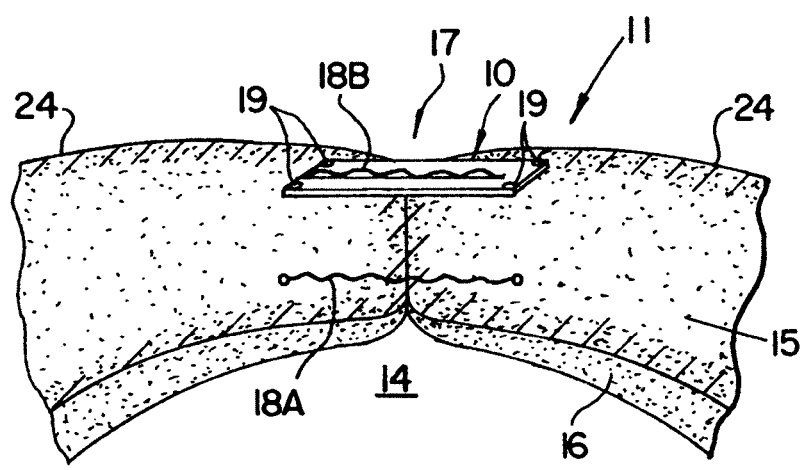
FIG. 5 is a cross-sectional side-view of a uterus hysterotomy closure using the embodiment of the device from FIG. 4A.
Figure 6:
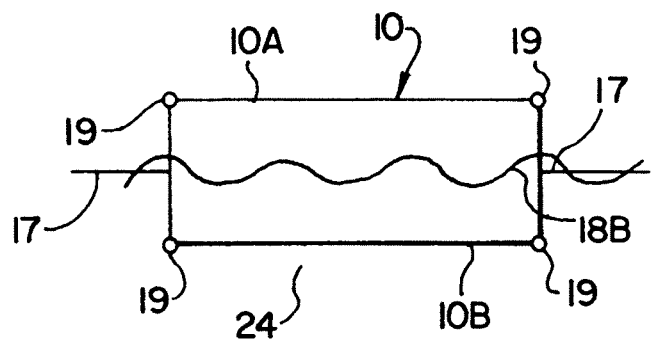
FIG. 6 is a top-view of the embodiment of the device shown in FIG. 4A.

FIG. 4A depicts an embodiment of the device. Graft 10 has proximal portion 10A and distal portion 10B and is shaped like a horizontal sheet. As depicted in FIGS. 5 and 6, graft 10 is placed over hysterotomy site 17. Graft is preferably made from four-layers of suitable collagenous material, although more or less layers may be used depending on the needs of the patient. Four layers are preferred because it should remodel into new tissue in about four weeks. This time period is desirable because the longer the graft remains in situ and not incorporated into the tissue matrix, the longer the material can act as a pathway for other tissues to migrate across its plane. Accordingly, if a later pregnancy was achieved 60-days after cesarean delivery, any remaining graft material present along the endometrial boarder could act as a conduit for proliferation of the placenta through the myometrium. Accordingly, it is desired that the graft material remodel quickly, but not in a way so as to disturb the involution of the postpartum uterus.

Suitable collagenous materials include, but are not limited to: purified or reconstituted collagen; porcine, bovine, or other mammalian pericardium; decellularized dermis; submucosa tissue such as urinary bladder submucosa, stomach submucosa, small intestine submucosa, and uterine submucosa; serosa tissue such as bovine serosa; basement membrane tissue such as liver basement membrane; autologous, allogenic, or xenogenic fascia lata; and so on. Materials which constitute a collagen-based extracellular matrix (ECM) are preferred. In general, mammalian tela submucosa tissues, which are collagen-based and thus predominantly collagen, are preferred ECM materials. These tissues may be procured from the alimentary, respiratory, urinary, or genital tracts of animals. Particularly suitable collagenous materials include ECMs such as submucosa, renal capsule membrane, dermal collagen, dura mater, pericardium, fascia lata, serosa, and peritoneum or basement membrane layers, including liver basement membrane. Suitable submucosa materials for these purposes include, for instance, intestinal submucosa, including small intestinal submucosa, stomach submucosa, urinary bladder submucosa, and uterine submucosa. Submucosa or other ECM tissue used in the invention is preferably highly purified, for example, as described in U.S. Pat. No. 6,206,931 to Cook et al., incorporated herein by reference in its entirety.

A preferred material is small intestine submucosa (SIS) obtained from a porcine source, although graft 10 is not limited to being made from SIS. Preferably, graft 10 includes an SIS material derived from porcine tela submucosa that is disinfected prior to delamination by the preparation disclosed in U.S. Patent Application Publication No. US2004/0180042A1 by Cook et al., published Sep. 16, 2004 and incorporated herein by reference in its entirety. Most preferably, the tunica submucosa of porcine small intestine is processed in this manner to obtain the ECM material. This method is believed to substantially preserve the aseptic state of the tela submucosa layer, particularly if the delamination process occurs under sterile conditions. Specifically, disinfecting the tela submucosa source, followed by removal of a purified matrix including the tela submucosa (e.g. by delaminating the tela submucosa from the tunica muscularis and the tunica mucosa), may minimize the exposure of the tela submucosa to bacteria and other contaminants. In turn, this enables minimizing exposure of the isolated tela submucosa matrix to disinfectants or sterilants if desired, thus substantially preserving the inherent biochemistry of the tela submucosa and many of the tela submucosa's beneficial effects.

Optionally, the ECM materials of graft 10 may be cross-linked by any suitable method. Cross-linked materials tend to be less bioresorbable than non-cross linked materials. Cross-linking agents can be used to form cross-linking regions within graft 10. Cross-linking can be provided by chemical and/or light-induced treatment of the material forming graft 10. Chemical cross-linking can also be used to join layers of material together. In a first aspect, a portion of graft 10 can be cross-linked by contacting graft 10 materials with a chemical cross-linking agent comprising glutaraldehyde, albumin, formaldehyde or a combination thereof. Other chemical cross-linking agents include epoxides, epoxyamines, diimides, and other difunctional/polyfunctional aldehydes. Cross-linking agents comprising aldehyde functional groups may be highly reactive with amine groups in proteins, such as collagen. Cross-linking agents may also include epoxyamines, which include both an amine moiety (e.g. a primary, secondary, tertiary, or quaternary amine) and an epoxide moiety. For example, an epoxyamine cross-linking agent can be a monoepoxyamine compound or a polyepoxyamine compound. Glutaraldehyde and polyepoxides are particularly preferred cross-linking agents for ECM materials. Alternatively, the material can be subjected to a form of energy to introduce cross-linking. For example, energy treatment suitable for use in the invention includes exposing the material to ultraviolet light, heat, or both. Cross-linking of natural polymers or synthetic polymers can also be accomplished with lyophilization, adhesives, pressure and or/heat.

In general, the process to form cross-linked material is conducted for a suitable amount of time. For example, the cross-linking agent may be allowed to penetrate through the material. Also, the cross-linking process generally reaches a point of completion at which time the properties of the material are essentially stable with respect to any additional measurable changes upon further contact with the cross-linking agent. Presumably, at completion, many, if not all, of the available functional groups of the material for cross-linking have reacted with a cross-linking agent. Since the formation of a fully cross-linked material is a slow process, the degree of cross-linking of the material at the cross-linking region can be selected to range from very low levels of cross-linking to complete cross-linking.

Additionally, graft 10 may be seeded with cells or biomolecules such as growth factors. In one example, the cells or biomolecules may be harvested from a healthy section of the individual's tissue, expanded in vitro using culture techniques, and seeded onto graft 10. In another example, chondrocytes for seeding into graft 10 can be obtained from other donor's tissues or from existing cell lines. Utilizing stem cell technology, mesenchymal cells obtained from bone marrow can also be differentiated into chondrocytes under appropriate culture conditions as described by, e.g., Butnariu-Ephrat et al., Clinical Orthopaedics and Related Research, 330:234-243, 1996. Graft 10 may also be seeded or doped with any other biomolecule or bioactive. ECM materials, when used, may naturally retain growth factors or other bioactive components native to the source tissue. For example, the submucosa tissue may include one or more growth factors such as basic fibroblast growth factor (FGF-2), transforming growth factor beta (TGF-beta), epidermal growth factor (EGF), and/or platelet derived growth factor (PDGF). As well, submucosa tissue used in the invention may include other biological materials such as heparin, heparin sulfate, hyaluronic acid, fibronectin and the like.

Graft 10 may also be formed from a tissue engineered product involving in vitro cell culture techniques, such as the use of stem cells or other cells in combination with SIS or other biodegradable material. One such technique is to seed cells onto SIS material or other biodegradable scaffold in the shape of graft 10. The term "biodegradable," as used herein refers to materials which dissipate within the body by any mechanism, including enzymatic or chemical degradation. Other biodegradable scaffolds, some of which are mentioned elsewhere, include collagen, extra-cellular matrix materials (ECM) such as SIS, and synthetic polymers such as polyglycolides, polylactides, and their co-polymers. Graft 10 may also be formed using stem cells. One technique is to culture stem cells in a specific environment to induce cell differentiation. The newly derived cells or tissue, created from stem cells, could be formed directly into graft 10 or seeded onto a scaffold material to form graft 10. Cell types used in this fashion include, but are not limited to, fibroblasts, smooth muscle cells, chondrocytes, and Leydig cells. The biodegradable scaffold material may be selected from any suitable biocompatible biodegradable polymer having the desired physical properties of resilience and absorptivity. Desirably, the biodegradable material includes polylactic acid (poly lactide) (PLA), polyglycolic acid (poly glycolide) (PGA), polylactic glycolic acid (poly lactide-co-glycolide) (PLGA), poly-4-hydroxybutyrate, poly-L-lactide (PLLA), polydioxanone, polygluconate, polylactic acid-polyethylene oxide copolymers, poly(hydroxybutyrate), polyanhydride, polyphosphoester, poly(caprolactone), polycarbonates, polyamides, polyanhydrides, polyamino acids, polyortho esters, polyacetals, polycyanoacrylates and degradable polyurethanes. The biodegradable scaffold material could also be an ECM material, such as SIS.

The terms "remodel" or "remodelable" as used herein refer to the ability of a material to allow or induce host tissue growth, proliferation or regeneration following implantation of the material in vivo. Remodeling can occur in various microenvironments within a body, including without limitation soft tissue, sphincter muscle region, tendon, ligament, bone tissues, and cardiovascular tissues. Upon implantation of a remodelable material, cellular infiltration and neovascularization are typically observed over a period of about five days to about six months or longer, as the remodelable material acts as a matrix for the ingrowth of adjacent tissue with site-specific structural and functional properties. The remodeling phenomenon which occurs in mammals following implantation of submucosal tissue includes rapid neovascularization and early mononuclear cell accumulation. Mesenchymal and epithelial cell proliferation and differentiation are typically observed by one week after in vivo implantation and extensive deposition of new extracellular matrix occurs almost immediately.

In addition, graft 10 may contain a plurality of perforations or holes allowing a portion of the resident tissue to contact another portion of the resident tissue through graft 10 and allow for tissue ingrowth. Perforated submucosal tissue graft constructs are further described in U.S. Pat. No. 5,997,575, which is incorporated by reference herein. Graft 10 may also contain a plurality of slits allowing a least a portion of the resident tissue to contact another portion of the resident tissue through graft 10 and allow for tissue ingrowth. Grafts having slits are further described in U.S. Patent Pub. No. 2005/021141, which is incorporated by reference herein.

Figure 4B:
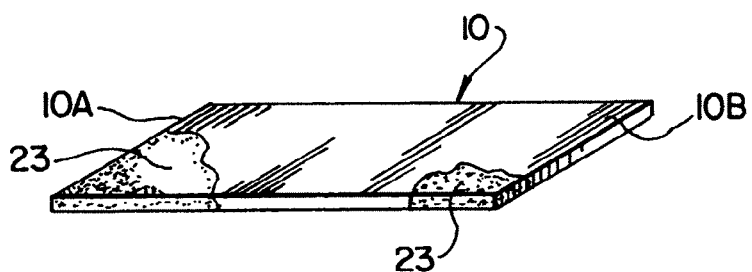
FIG. 4B is an alternate perspective view of an embodiment of the device shown in FIG. 4A.

In addition, graft 10 may be partially or entirely covered with coating 23 as depicted in FIG. 4B. Coating 23 can also be loaded with a variety of bioactives. Coating 23 is capable of releasing the bioactive into the body at a predetermined time and at a predetermined rate. Such polymeric coatings include drug-eluting matrix materials described in U.S. Pat. Nos. 5,380,299, 6,530,951, 6,774,278 and U.S. patent application Ser. Nos. 10/218,305, 10/223,415, 10/410,587, 10/000,659, and 10/618,977, all of which are incorporated in their entirety herein by reference. Alternatively, different drug-eluting polymer coatings can be coated onto graft 10 as well. Coating 23 can include any bioactive commonly known to those skilled in the art to help reduce tissue irritation incurred as a result of graft 10 being in contact with tissue for a prolonged period of time.

Accordingly, coating 23 may include rifampin and minocycline, or other antibiotic/antimicrobial drugs. These drugs may include, but are not limited to, a mixture of rifampin and minocycline, a non-steroidal anti-inflammatory drug (NSAID) (including, but not limited to, aspirin, salsalate, diflunisal, ibuprofen, ketoprofen, nabumetone, piroxicam, naproxen, diclofenac, indomethacin, sulindac, tolmetin, etodolac, ketorolac, oxaprozin, and celecoxib), a penicillin, a cephalosporin, a carbepenem, a beta-lactam, an antibiotic, a macrolide, a lincosamide, an aminoglycoside, a glycopeptide, a tetracyline, a chloramphenicol, a quinolone, a fucidin, a sulfonamide, a trimethoprim, a rifamycin, an oxaline, a streptogramin, a lipopeptide, a ketolide, a polyene, an azole, an echinocandin, alpha-terpineol, methylisothiazolone, cetylpyridinium chloride, chloroxyleneol, hexachlorophene, chlorhexidine and other cationic biguanides, methylene chloride, iodine and iodophores, triclosan, taurinamides, nitrofurantoin, methenamine, aldehydes, azylic acid, rifampycin, silver, benzyl peroxide, alcohols, carboxylic acids and salts, and silver sulfadiazine. Other examples of suitable antibiotics include amoxicillin, trimethoprim-sulfamethoxazole, azithromycin, clarithromycin, amoxicillin-clavulanate, cefprozil, cefuroxime, cefpodoxime and cefdinir. Anti-rejection drugs help to prevent rejection of the transplant by the body. Anti-rejection drugs may include, but are not limited to, neomycin, cyclosporine, prednisone, and tacrolimus.

Graft 10 may be loaded with penicillin by dipping graft 10 in a suitable liquid medium containing HAMM's F12 medium (Gibco, New York, N.Y.) containing 10% fetal bovine serum with L-glutamine (292 µg/ml), penicillin (100 µg/ml) and ascorbic acid (50 µg/ml). Other media may also be used. For example, "standard cell growth media" may include Dulbecco's Modified Eagles Medium, low glucose (DMEN), with 110 mg/L pyruvate and glutamine, supplemented with 10-20% Fetal Bovine Serum (FBS) or 10-20% calf serum (CS) and 100 U/mi penicillin. Other standard media include Basal Medium Eagle, Minimal Essential Media, McCoy's 5A Medium, and the like, preferably supplemented as above (commercially available from, e.g., JRH Biosciences, Lenexa, Kans.; GIBCO, BRL, Grand Island, N.Y.; Sigma Chemical Co., St. Louis, Mo.). Graft 10 may also be treated with sex based hormones including, but not limited to, prostaglandins. Methods for doping graft 10 include, but are not limited to, dipping or soaking interior 10 into a suitable drug solution. Any other suitable method for doping graft 10 with drugs can also be used.

Graft 10 is preferably 10 cm long and 4 cm wide; however, other dimensions are contemplated depending upon the needs of the patient and the size of the wound to be repaired. As depicted in FIG. 5, hysterotomy site 17 is closed using a two-layer running suture 18A, 18B. First-layer suture 18A is used to reconnect myometrium 15. Graft 10, having a first and second portion, is then laid onto visceral peritoneum 24 and second-layer suture 18B is used to reconnect uterine myometrium 15 and attach graft 10 to incision site 17. Graft 10 is tacked down using tacking sutures 19 to help graft 10 remain in place. Because graft 10 is laid onto visceral peritoneum 24, over incision site 17, and included in second-layer suture 18B, it will remodel into like uterine cells and should create a stronger hysterotomy closure than using traditional suturing methods alone that result in a reduced-strength closure site. FIG. 6 depicts a top-view of hysterotomy incision 17 after being closed and having graft 10 sewn into place onto visceral peritoneum 24.

Figure 7:
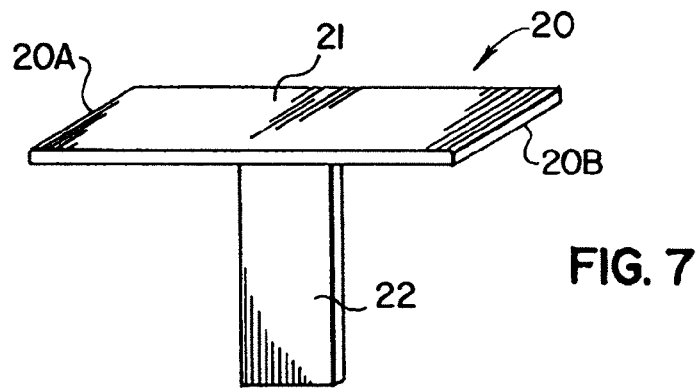
FIG. 7 is a perspective view of an embodiment of the device.

FIG. 7 depicts another embodiment of the device. Graft 20 is like graft 10, but formed into a different shape. Graft 20 is shaped like a "T" having a proximal portion 20A, a distal portion 20B, and upper portion 21, and a lower portion 22. Lower portion 22 of graft 20, having a first and second portion, is preferably 10 cm long and 1.5 cm wide and upper portion 21 of graft 20 is 10 cm long and 4 cm wide; however, other dimensions are contemplated depending upon the needs of the patient and the size of the wound to be repaired. Additionally, an optional coating, described above, may be applied to graft 20.

Figure 8:
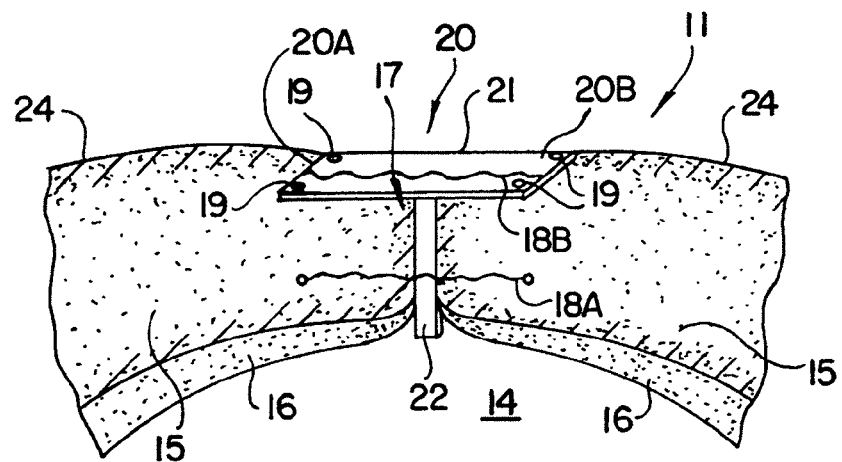
FIG. 8 is a cross-sectional side-view of a uterus hysterotomy closure using the embodiment of the device from FIG. 7.
Figure 9:
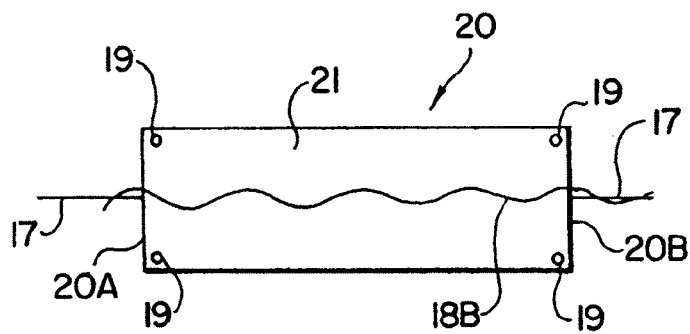
FIG. 9 is a top-view of the embodiment of the device shown in FIG. 7.

As depicted in FIG. 8, before hysterotomy site 17 is closed, graft 20 is placed into hysterotomy site 17 so that lower portion 22 is placed near endometrium 16 and myometrium 15, and upper portion 21 covers visceral peritoneum 24. First-layer closure 18A is then sewn connecting each side of myometrium 15 with lower portion 22 of graft 20. As depicted in FIGS. 8 (cross-sectional side view) and 9 (top-view), second-layer suture 18B is then sewn into place connecting each side of myometrium 15 and visceral peritoneum 24 with upper portion 21 of graft. Proximal portion 20A and distal portion 20B of graft 20 is tacked into visceral peritoneum 24 of uterus 11 using tacking stitches 19.

Figure 10:
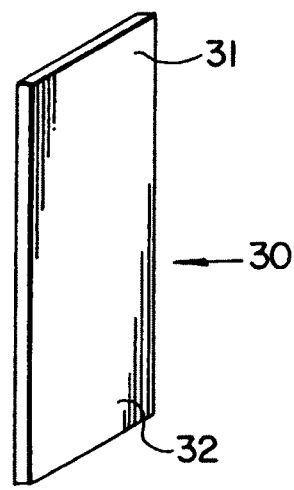
FIG. 10 is a perspective view of an embodiment of the device.

As depicted in FIG. 10, graft 30 is another embodiment of the device like graft 10 but used as a vertical sheet. Graft 30, having a first and second portion, is preferably 10 cm long and 1.5 cm wide; however, other dimensions are contemplated depending upon the needs of the patient and the size of the wound to be repaired. Additionally, an optional coating, described above, may be applied to graft 30.

Figure 11:
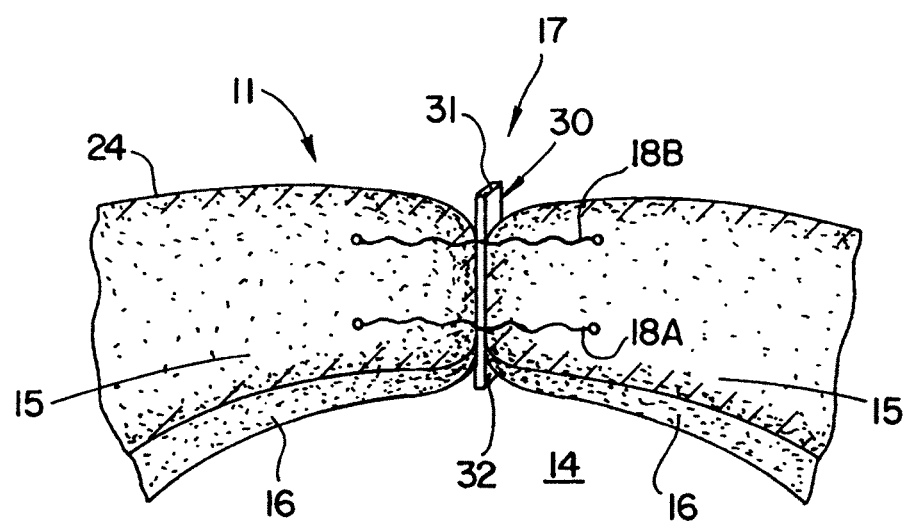
FIG. 11 is a cross-sectional side-view of a uterus hysterotomy closure using the embodiment of the device from FIG. 10.

As depicted in FIG. 11, graft 30 is placed vertically into hysterotomy site 17 such that lower portion 32 resides near endometrium 16 and myometrium 15. The first edge and second portion each touch a side of the wound. First-layer closure 18A is then sewn connecting each side of myometrium 15 with lower portion 32 of graft 30. Second-layer suture 18B is then sewn connecting each side of myometrium 15 with upper portion 31 of graft 30.

Figure 12:
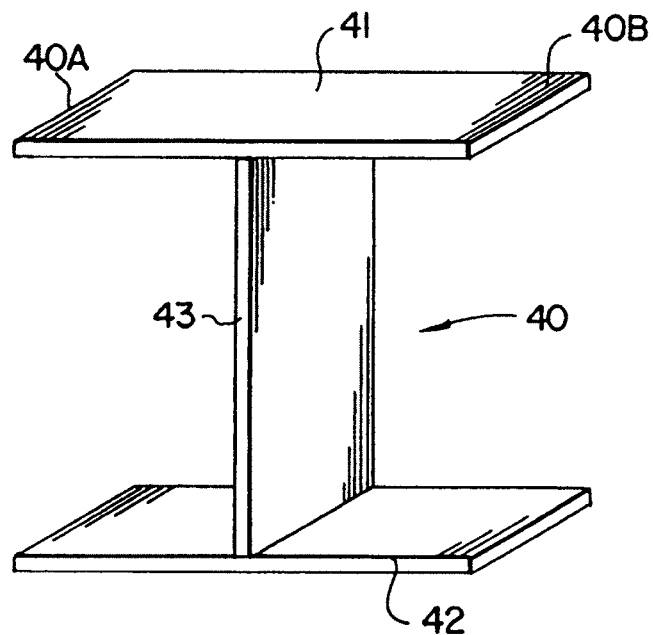
FIG. 12 is a perspective view of an embodiment of the device.

FIG. 12 depicts yet another embodiment of the device. Graft 40 is like graft 10, but formed into a different shape. Graft 40 is shaped like an "I" having a proximal portion 40A, a distal portion 40B, and upper portion 41, a lower portion 42, and an intermediate portion 43, having a first and second portion. Upper portion 41 and lower portion 42 of graft 40 are preferably 10 cm long and 4 cm wide; intermediate portion 43 is preferably 10 cm long and 2 cm wide; however, other dimensions are contemplated depending upon the needs of the patient and the size of the wound to be repaired. Additionally, an optional coating, as described above, may be applied to graft 40.

Figure 13:
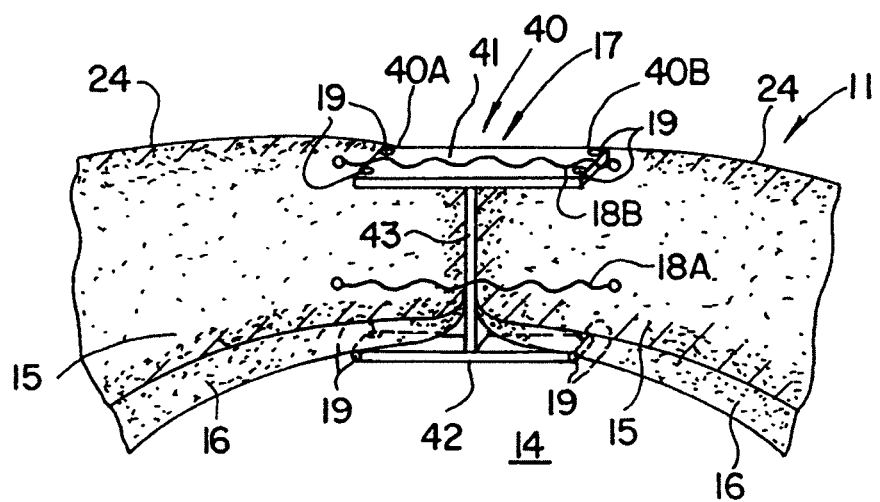
FIG. 13 is a cross-sectional side-view of a uterus hysterotomy closure using the embodiment of the device from FIG. 12.

As depicted in FIG. 13, before hysterotomy site 17 is closed, graft 40 is placed into hysterotomy site 17 so that lower portion 42 is in communication with enodmetrium 16, intermediate portion 43 is in communication with enodmetrium 16 and myometrium 15, and upper portion 41 covers visceral peritoneum 24. Tacking sutures 19 are used to connect lower portion 42 to enodmetrium 16. First-layer suture 18A is then sewn into place connecting each side of enodmetrium 16 and myometrium 15 with intermediate portion 43 of graft 40. Second-layer suture 18B is then sewn into place connecting each side of myometrium 15 and visceral peritoneum 24 with upper portion 41 of graft. Proximal portion 40A and distal portion 40B of upper portion 41 are tacked into visceral peritoneum 24 of uterus 11 using tacking stitches 19. Graft 40 encourages cell proliferation along two planes involving two tissue types: fibroblastic serosa and highly vascular decidua.

Figure 14:
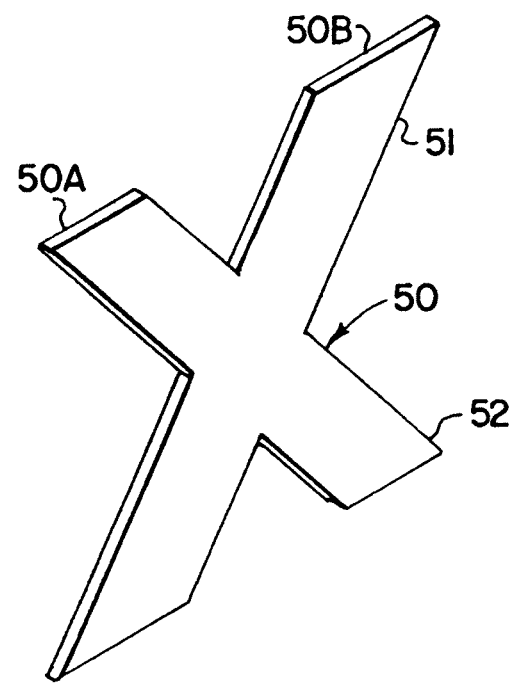
FIG. 14 is a perspective view of an embodiment of the device.

FIG. 14 depicts yet another embodiment of the device. Graft 50 is like graft 10, but formed into a different shape. Graft 50 is shaped like an "X" having a proximal portion 50A, a distal portion 50B, and upper portion 51, and a lower portion 52. Graft 50 is preferably 10 cm long and 2 cm wide; however, other dimensions are contemplated depending upon the needs of the patient and the size of the wound to be repaired. Additionally, an optional, coating as described above, may be applied to graft 50.

Figure 15:
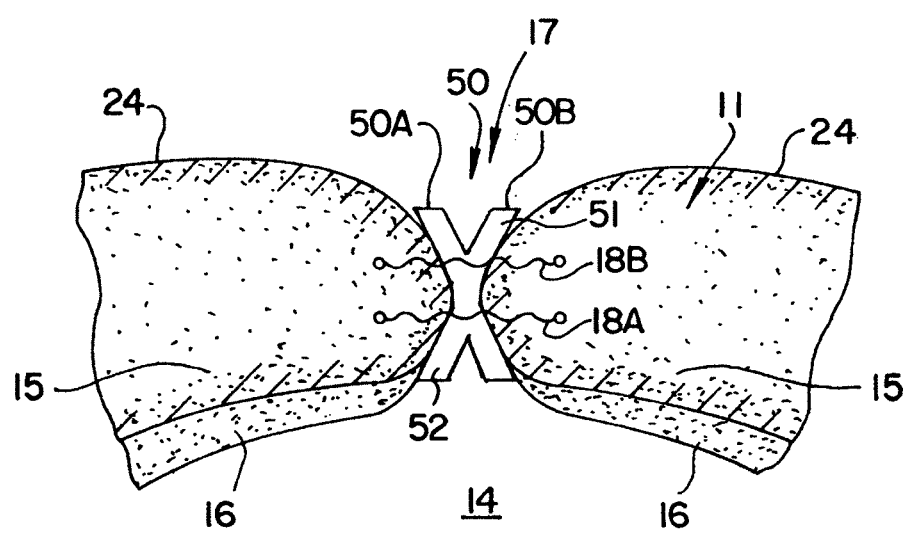
FIG. 15 is a cross-sectional side-view of a uterus hysterotomy closure using the embodiment of the device from FIG. 14.

As depicted in FIG. 15, before hysterotomy site 17 is closed, graft 50 is placed into hysterotomy site 17 so that lower portion 52 is in communication with enodmetrium 16 and myometrium 15, and upper portion 51 is in communication with visceral peritoneum 24 and myometrium 15. First-layer suture 18A is then sewn into place connecting each side of myometrium 15 with lower portion 52 of graft 50. Second-layer suture 18B is then sewn into place connecting each side of myometrium 15 and visceral peritoneum 24 with upper portion 51 of graft. Graft 50 allows for the use of apposition of all layers and creates a double layer interface between the myometrial edges.

Figure 16:
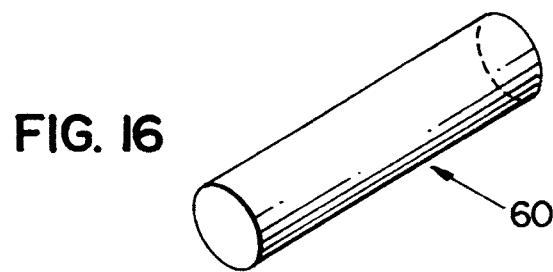
FIG. 16 is a perspective view of an embodiment of the device.

FIG. 16 depicts yet another embodiment of the device. Graft 60 is like graft 10 but formed into a tube-shape from suitable collagenous material foam. Graft 60 is preferably 10 cm long and has a diameter of 0.5 cm; however, other dimensions are contemplated depending upon the needs of the patient and the size of the wound to be repaired. Additionally, an optional coating, as described above, may be applied to graft 60.

Figure 17:
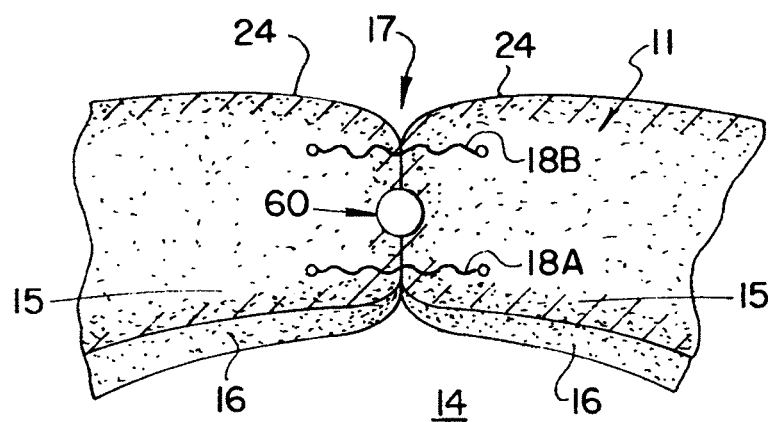
FIG. 17 is a cross-sectional side-view of a uterus hysterotomy closure using the embodiment of the device from FIG. 16.

As depicted in FIG. 17, first-layer suture 18A is sewn into place connecting each side of myometrium 15 with graft 60. Graft 60 is placed into hysterotomy site 17 and second-layer suture 18B is then sewn into place attaching both sides of myometrium 16 and visceral peritoneum 24.

Figure 18:
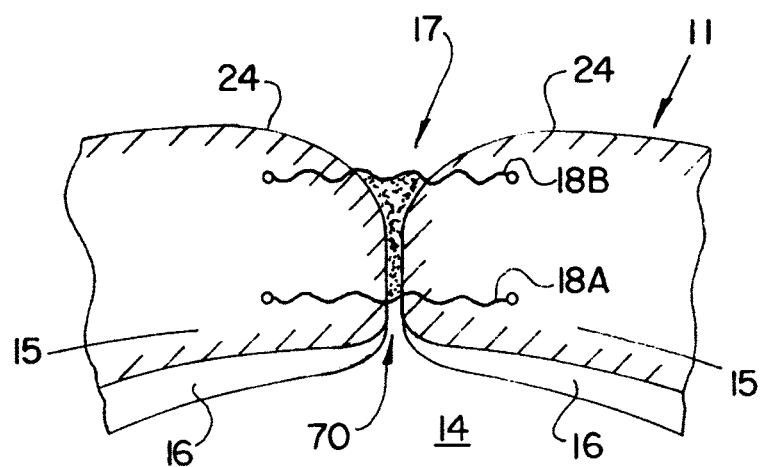
FIG. 18 is a cross-sectional side-view of a uterus hysterotomy closure using the embodiment of the device.

FIG. 18 depicts yet another embodiment of the device. Graft 70 is made from a suitably collagenous material gel suspension. Collagenous material gels are described in U.S. Pat. Nos. 5,866,414, 5,516,533, U.S. patent application Ser. No. 10/569,218 filed Feb. 24, 2006 entitled "Graft Materials Containing Bioactive Substances, and Methods for Their Manufacture," and W.O. 2005020847, all of which are incorporated in their entirety herein by reference. First-layer suture 18A is used to connect myometrium 15. Before adding second-layer suture 18B, graft 70 is applied into hysterotomy site 17. Second-layer suture 18B is then used to close hysterotomy site 17.

EXAMPLE 1

Cesarean sections were performed on two sheep and the hysterotomies were closed in four sections. One section was closed with a running suture and no graft to serve as a control area for standard healing. A second section was closed with a soft tissue graft available from Cook, sold under the trade name Surgisis, over the top of the incision (overlay) with sutures holding it down on the incision. A third section was closed with a soft tissue graft available from Cook, sold under the trade name Surgisis, that was incorporated into the suture line in a roughly vertical or transmural orientation and over the top by using a two-layer graft that was shaped as a "T" in cross-section with the stem of the T protruding into the incision line. The fourth section was closed in identical fashion to the third section except that the stem of the T has fenestrations (slits) cut into it to potentially aid in tissue growth across it.

Histological results at three months post-implant showed good healing in the control sections with some evidence of mucosa defects and wall thin areas. The overlay sections showed slight improvement in healed tissue stratification but still showed thin areas in the wall. No differences were observed between the two T groups, but the tissues around the T's were less well-healed, more disorganized, but considerably thicker-walled than the other areas.

As is evident, the embodiments provide an effective solution for strong hysterotomy closure repair. However, it is contemplated that which is disclosed herein can also be applied to different types of wound repair, including but not limited to laparotomy and hysterotomy closures, full thickness lacerations, endoscopic port closures, and surgical and repair sites on other parts of the body or extremities.

The foregoing description and drawings are provided for illustrative purposes only and are not intended to limit the scope of the invention described herein or with regard to the details of its construction and manner of operation. It will be evident to one skilled in the art that modifications and variations may be made without departing from the spirit and scope of the invention. Changes in form and in the proportion of parts, as well as the substitution of equivalents, are contemplated as circumstances may suggest and render expedience; although specific terms have been employed, they are intended in a generic and descriptive sense only and not for the purpose of limiting the scope of the invention set forth in the following claims.

What is claimed is:

1. The use of a biological tissue graft that has been rendered non-cellular, in the manufacture of a medicament for treating a hysterotomy incision by interposing the biological tissue graft between two tissue faces created by the hysterotomy incision.

2. The use of claim 1, wherein the biological tissue graft comprises submucosa.

3. A method for repairing a hysterotomy site comprising:
   providing a graft, wherein the graft comprises at least one collagenous material capable of remodeling;
   interposing the graft between a first incised tissue face and a second incised tissue face of the the hysterotomy site;
   attaching the graft to the first and second incised tissue faces of the hysterotomy site; and
   closing the hysterotomy site.

4. The method of claim 3, wherein the closing the hysterotomy site further comprises using a suture, staple, or glue.

5. The method of claim 3, wherein the graft is seeded with cells, biomolecules, or bioactives.

6. The method of claim 3, wherein the graft further comprises a coating.

7. The method of claim 3, wherein the collagenous material comprises a suspension, gel or a foam tube.

* * * * *